(12) United States Patent

Baca

(10) Patent No.: US 12,622,614 B2

(45) Date of Patent: May 12, 2026

(54) BLOOD ANALYTE LEVEL MEASUREMENT DEVICE

(71) Applicant: Baca Bio-Holdings, LLC, Pharr, TX (US)

(72) Inventor: Americo M Baca, Pharr, TX (US)

(73) Assignee: Baca-Bio Holdings, LLC, Pharr, TX (US)

( * ) Notice: Subject to any disclaimer, the term of this patent is extended or adjusted under 35 U.S.C. 154(b) by 1017 days.

(21) Appl. No.: 17/829,245

(22) Filed: May 31, 2022

(65) Prior Publication Data

US 2023/0380732 A1 Nov. 30, 2023

(51) Int. Cl.
 *A61B 5/1455* (2006.01)
 *A61B 5/00* (2006.01)

(52) U.S. Cl.
 CPC ........ *A61B 5/14558* (2013.01); *A61B 5/6826* (2013.01)

(58) Field of Classification Search
 CPC . A61B 5/14558; A61B 5/6826; A61B 5/1495; A61B 5/14546; A61B 5/0075; A61B 5/14532
 See application file for complete search history.

(56) References Cited

U.S. PATENT DOCUMENTS

| | | | | | |
|---|---|---|---|---|---|
| 5,218,207 A | * | 6/1993 | Rosenthal | ............ | G01N 21/359 |
| | | | | | 250/341.1 |
| 5,687,721 A | * | 11/1997 | Kuhls | ................ | A61B 5/14558 |
| | | | | | 600/316 |

* cited by examiner

*Primary Examiner* — Abid A Mustansir

(74) *Attorney, Agent, or Firm* — Invention Matters, LLC; Edwin De Angel

(57) ABSTRACT

Disclosed is a device for non-invasive measurement of at least one blood analyte level in a user. The device comprises a light arrangement to emit a light beam with a first wavelength towards a body part of the user, a filtering unit to be arranged to receive the light beam passed through the body part of the user, with a polarized filter configured to be displaced between a base position and a target position, a measuring arrangement to measure an angle of the polarized filter, a sensor arranged to receive the light beam passed through the polarized filter, and generate a block signal in response to blockage of the light beam to be received thereat, and a control unit configured to determine the blood analyte level based on the measured angle of the polarized filter at the target position thereof in response to receipt of the block signal.

4 Claims, 3 Drawing Sheets

100

108

102

104

S

106

110

BLOOD ANALYTE LEVEL MEASUREMENT DEVICE

TECHNICAL FIELD

The present disclosure relates to systems, methods and devices for measuring blood analyte levels; and specifically, to a device for measuring blood analyte levels in a user.

BACKGROUND

In recent years, increasing growth in technology has led to rapid development of various types of systems, methods, devices and services, across a spectrum of fields including, but not limited to, medicine, diagnostics, manufacturing, robotics and the like. Such systems or devices may be utilized. Such devices are required by millions of users worldwide, such as by medical personnel or by self-employed by the users in a variety of scenarios such as medical check-ups, patient-care or hospitality, self-diagnosis via user and so forth.

Conventionally, the measurement of the blood analyte level (such as, blood glucose) is done in an invasive manner such as, finger-prick methods that require a sample of blood of a user, for further testing thereof. To solve the aforementioned problem, different devices and/or methods are proposed as non-invasive, including, but not limited to, methods for blood analyte level measurements via laser exposure such as, surface plasmon resonance (SPR), optical polarimetry etc., methods for blood analyte level measurements via different spectroscopy methods such as, near infrared spectroscopy, optical coherence tomography, raman spectroscopy, and other similar methods for blood analyte level measurements. However, such methods and systems are highly complex and expensive to manufacture and thus, scaling for the general population is not feasible. Consequently, a need for a simple, effective and cost-effective device, system or method for measuring the blood analyte level in a non-invasive manner is developed.

Therefore, in light of the foregoing discussion, there exists a need to overcome the aforementioned drawbacks associated with the conventional systems and provide an improved device for non-invasive measurement of at least one blood analyte level in a user.

SUMMARY OF THE INVENTION

The present disclosure seeks to provide a device for non-invasive measurement of at least one blood analyte level in a user. An aim of the present disclosure is to provide a solution that overcomes at least partially the problems encountered in prior art.

In an aspect, an embodiment of the present disclosure provides a device for non-invasive measurement of at least one blood analyte level in a user, the device comprising:

a light arrangement configured to emit a light beam with a first wavelength, the light arrangement adapted to be arranged to emit the light beam towards a body part of the user;

a filtering unit adapted to be arranged to receive the light beam passed through the body part of the user, the filtering unit comprising a polarized filter configured to be displaced between a base position and a target position, wherein the filtering unit is configured to block the light beam received directly from the light arrangement at the base position thereof and to block the light beam received after passing through the body part of the user at the target position thereof;

a measuring arrangement configured to measure an angle of the polarized filter at the target position with respect to the base position thereof;

a sensor arranged to receive the light beam passed through the polarized filter, the sensor configured to generate a block signal in response to blockage of the light beam to be received thereat; and a control unit in signal communication with the measuring arrangement to receive value of the measured angle of the polarized filter at the target position with respect to the base position thereof, and in signal communication with the sensor to receive the block signal indicative of the blockage of the light beam thereat, wherein the control unit is configured to determine the at least one blood analyte level in the said body part of the user based on a value of the measured angle of the polarized filter at the target position thereof in response to receipt of the block signal.

Embodiments of the present disclosure substantially eliminate or at least partially address the aforementioned problems in the prior art, and enable automation of the blood analyte level measurement in a simple, quick, efficient and non-invasive manner.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

Figure 1:
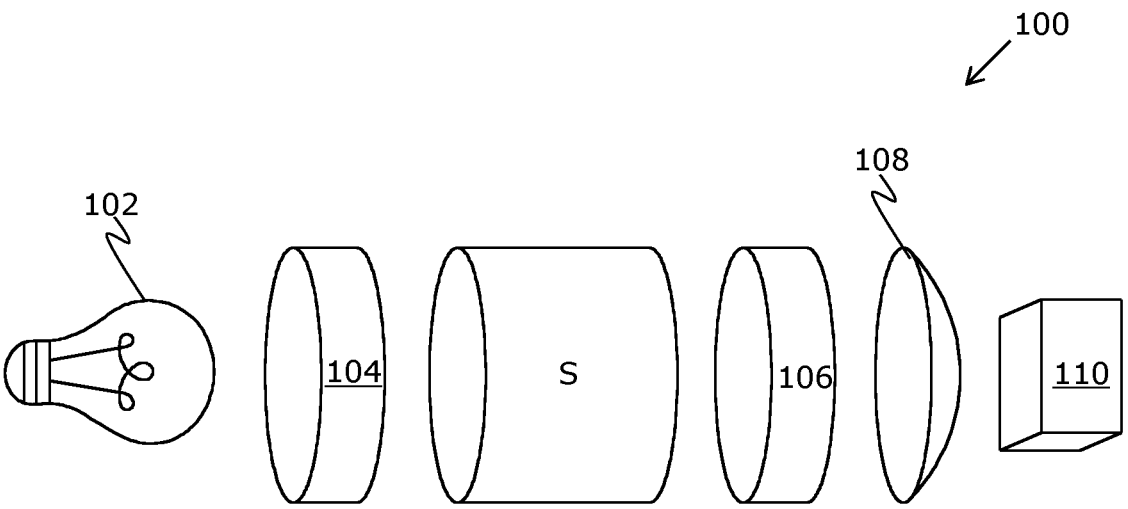
FIG. 1 is a schematic illustration of a device for non-invasive measurement of at least one blood analyte level in a user, in accordance with various embodiments of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In one aspect, an embodiment of the present disclosure provides a device for non-invasive measurement of at least one blood analyte level in a user, the device comprising:

a light arrangement configured to emit a light beam with a first wavelength, the light arrangement adapted to be arranged to emit the light beam towards a body part of the user;

a filtering unit adapted to be arranged to receive the light beam passed through the body part of the user, the filtering unit comprising a polarized filter configured to be displaced between a base position and a target position, wherein the filtering unit is configured to block the light beam received directly from the light arrangement at the base position thereof and to block the light beam received after passing through the body part of the user at the target position thereof;

a measuring arrangement configured to measure an angle of the polarized filter at the target position with respect to the base position thereof;

a sensor arranged to receive the light beam passed through the polarized filter, the sensor configured to generate a block signal in response to blockage of the light beam to be received thereat; and a control unit in signal communication with the measuring arrangement to receive value of the measured angle of the polarized filter at the target position with respect to the base position thereof, and in signal communication with the sensor to receive the block signal indicative of the blockage of the light beam thereat, wherein the control unit is configured to determine the at least one blood analyte level in the said body part of the user based on a value of the measured angle of the polarized filter at the target position thereof in response to receipt of the block signal.

The present disclosure provides a device for non-invasive measurement of at least one blood analyte level in a user. The device for non-invasive measurement refers to a device configured to be shaped to accommodate at least a body part of the user and to provide a non-invasive alternative to conventional invasive blood analyte level measurement systems and/or devices. The term "analyte" refers to a substance or chemical constituent determined in an analytical procedure, such as blood testing. In an example, in an immunoassay, the analyte may be a ligand or binder, while in blood glucose testing, the analyte is glucose. Currently, existing devices and/or methods configured for measuring the at least one blood analyte level lack the capacity and/or efficiency to accommodate the general population in a non-invasive manner. To solve the aforementioned problem, different devices and/or methods are proposed as non-invasive, including, but not limited to, methods for blood analyte level measurements via laser exposure such as, surface plasmon resonance (SPR), optical polarimetry etc., methods for blood analyte level measurements via different spectroscopy methods such as, near infrared spectroscopy, optical coherence tomography, raman spectroscopy, photoacustic spectroscopy, thermal emission spectroscopy etc., methods for blood analyte level measurements via fluorescence methodology, methods for tissue thickness measurement via ultrasound methodology and the like. However, current methods and systems are highly complex, expensive to manufacture and thus, non-scalable for a huge population and consequently, a need for a simple, accurate and efficient and cost-effective device or method for measuring the blood analyte level in a non-invasive manner is developed. Thus, in light of the aforementioned problems, the present disclosure provides the device for non-invasive measurement of the at least one blood analyte level in the user that is simple, efficient, and inexpensive in construction and implementation and thereby highly scalable for a huge population.

In one or more embodiments, the measured at least one blood analyte level comprises at least one of a blood glucose level, HbgA1c levels. Typically, the device for non-invasive measurement of the at least one blood analyte level is implemented for measuring at least one of blood glucose levels, HbgA1c levels. The HbgA1c (or Hemoglobin A1c) levels are associated with average levels of blood glucose over a time period such as, one month, two months or three months. However, it will be appreciated that the device may be employed to determine other blood analyte levels without limiting the scope of the present disclosure.

The device comprises a light arrangement configured to emit a light beam with a first wavelength, the light arrangement adapted to be arranged to emit the light beam towards a body part of the user. Herein, the term "light arrangement" refers to a light source configured to emit the light beam, i.e., an electrically and/or electronically operated device that is configured to emit light beam therefrom. Optionally, the at least one light source comprises at least one of a LED light, an incandescent light, a monochromatic light, an infrared light, a laser or a combination thereof. The device beneficially employs polarimetry to measure the blood analyte level in a particular tissue, or substance. Notably, the device employs the combined application of light beams having an appropriate wavelength (i.e., the first wavelength) from the light arrangement towards the body part of the user. Moreover, the device is configured to be shaped to allow the light arrangement to emit the light beam to the desired tissue with close contact, such that the body part may refract and absorb the incident light beam while allowing the device (such as, via a sensor) to pick up the remnant signal to measure the at least one blood analyte level.

In one or more embodiments, the first wavelength of the light beam is in a range of 560 nanometers to 890 nanometers (nm). The emitted light beam from the light arrangement is typically in the range of 560 nm to 890 nm. Such a wavelength range is obtained through various experimentations and procedures and is determined suitable for measuring the at least one blood analyte level via the device. For example, the first wavelength of the light beam may vary from 560 nm, 570 nm, 580 nm, 590 nm, 600 nm, 650 nm, 700 nm, 750 nm, 790 nm up to 660 nm, 670 nm, 680 nm, 690 nm, 700 nm, 750 nm, 800 nm, 850 nm, 890 nm.

In one or more embodiments, the light arrangement is configured to emit the light beam directly and/or indirectly towards the body part of the user, wherein the body part of the user is at least one of an eye, an ear lobe, a finger. The light beam is either emitted directly towards the body part of the user or indirectly upon passing through one or more optical elements. Typically, the light arrangement may direct the light beam towards the optical element (such as, a polarized filter) to beneficially utilize the chirality of the molecules and obtain a light beam having a desired polarization.

In one or more embodiments, the light arrangement comprises at least one light source configured to emit a spectrum of electromagnetic radiation and a filter configured selectively pass the light beam from the spectrum of electromagnetic radiation with the first wavelength. Herein, the term "filter" refers to a polarized filter configured to selectively pass the light beam having a specified polarization. The filter allows light beams of a specific polarization or wavelength to pass through while blocking light waves of other polarizations or wavelengths. Typically, the filter is configured for filtering the incident spectrum of electromagnetic radiation having the first wavelength and blocking other wavelengths of the electromagnetic radiation. Beneficially, the filter enables the incident spectrum of electromagnetic radiation of undefined or mixed polarization into a beam of well-defined polarization i.e., a polarized light beam.

The device further comprises a filtering unit adapted to be arranged to receive the light beam passed through the body part of the user, the filtering unit comprising a polarized filter configured to be displaced between a base position and a target position. The term "filtering unit" refers to a module of the device configured to block the incident light beam at specified orientations. The filtering unit comprises the polarized filter configured to be displaced between the base position and the target position. The term "base position" refers to an initial blocking configuration of the polarized filter, wherein the body part of the user is not placed between the light arrangement and the filtering unit. Herein, the filtering unit is configured to block the light beam received directly from the light arrangement at the base position thereof. Alternatively stated, without the presence of the body part of the user for measurement via the device, the polarized filter is configured to block the incident light beam at the base position. Moreover, the filtering unit is configured to block the light beam received after passing through the body part of the user at the target position thereof. The term "target position" refers to a final blocking configuration of the polarized filter, wherein the body part of the user is placed between the light arrangement and the filtering unit.

Herein, upon analyzing the behaviour of electromagnetic properties of the light beam from the light source i.e., behaviour of the light beam of a determined wavelength (such as, the first wavelength between 560 nm-890 nm), passing through any substance (such as, the body part of the user), the blood analyte level may be determined. Typically, as the light beam goes through the body part and travels via the filtering unit, at certain angles the light is blocked. Moreover, as the polarized filter is displaced or rotated, different angles with each different user are obtained. In operation, as the light arrangement is applied to the body part of the user, the body part being analyzed is lit due to the incident light beam sufficient to be carried to a sensor upon modification via the polarized filter. The polarized filter is rotated in a clockwise manner, such that initially the polarized filter at the zero-degree angle blocks all incident light applied via the light arrangement. Further, as the polarized filter is rotated, at certain angles the light beam passing through is consequently blocked and thereby the angle rotated by the polarized filter from the base position to the target position is measured to enable measurement of the at least one blood analyte level. Moreover, based on the law of optical rotation, the device allows measurement of different angles for different blood analyte levels of the user.

In one or more embodiments, the filtering unit further comprises a motor arrangement configured to displace the polarized filter between the base position and the target position thereof. The term "motor arrangement" refers to the multiple electrical and mechanical components interconnected to perform the function of displacing the polarized filter. The motor arrangement comprises at least an electric motor, mechanically coupled with the polarized filter, configured to convert electrical energy (from any power source such as, a battery) into mechanical energy for displacing the coupled polarized filter. The motor arrangement is configured to displace a position and/or an orientation of the polarized filter for enabling blocking of the light beam thereof. The motor arrangement may comprise different types of gears, shafts, and connectors for enabling mechanical coupling and thereby the displacement of the polarized filter in a required manner.

In one or more embodiments, the motor arrangement is configured to displace the polarized filter by performing at least one of an angular displacement, a linear displacement of the polarized filter. The motor arrangement is configured to displace the polarized filter to change at least one of the position or the orientation of the polarized filter. Herein, the motor arrangement performs the linear displacement to change the position of the polarized filter. For example, the polarized filter is displaced by 3 millimeters for a required implementation. Moreover, the motor arrangement performs the angular displacement to change the orientation of the polarized filter. Typically, the polarized filter may be angularly displaced (or rotated) about a central axis or tilted (by a combination of linear and angular displacements) at specific angles about the central axis, of the polarized filter based on the implementation of the device. Beneficially, the linear displacement is performed to focus and effectively receive the remnant light beam passing through the body part of the user whereas the angular displacement is performed to block the incident light beam at the target position.

Optionally, the polarized filter is displaced by an angular displacement of 0 degree and/or a linear displacement of 0 millimeter at the base position. Moreover, optionally, the polarized filter is displaced by an angular displacement in a range of 0 degree to 90 degrees and/or a linear displacement in the range of 0 millimeters to 50 millimeters at the target position. Typically, to achieve the target position that blocks the incident light beam upon passing through the body part of the user, the motor arrangement gradually and continuously performs at least one of the linear displacement and the angular displacement of the polarized filter until the incident light beam is blocked. For example, the motor arrangement performs an angular displacement of 60 degrees to block the incident light beam.

The device further comprises a measuring arrangement configured to measure an angle of the polarized filter at the target position with respect to the base position thereof. The "measuring arrangement" refers to one or more electrical and/or mechanical components arranged to measure at least the current position and orientation of the polarized filter. The measuring arrangement may be any angle measuring instrument including, but not limited to, a digital angle finder, a mechanical protractor, a sine bar, an angular gauge, a digital protractor, an inclinometer, a digital level and the like. Upon measuring the angle of the polarized filter at the target position with respect to the base position thereof, the measured angle is utilized to measure the at least one blood analyte level as described earlier in the present disclosure.

The device further comprises a sensor arranged to receive the light beam passed through the polarized filter, the sensor configured to generate a block signal in response to blockage of the light beam to be received thereat. The "sensor" refers to a type of light sensor configured to detect the blockage of the light beam via the polarized filter at the target position and correspondingly generate the block signal for further operation. Herein, the block signal may be used by the measuring arrangement to measure the current position and orientation of the polarized filter on receipt of the block signal. The sensor includes at least one of a photoresistor, a phototransistor, a photodiode, a light proximity sensor, a photo-voltaic devices, a light-dependent sensor, a pyro-electric sensor and the like. In an example, the sensor is a UV optimized sensor. Additionally, optionally, the sensor is further configured to measure one or more characteristics of the received light beam, including an intensity of the received light beam, a wave speed of the received light beam, a wavelength of the received light beam, an angle of the received light beam. The "one or more characteristics" of the received light beam refer to characteristic properties of the light beam including the intensity, wave speed, wavelength and the angle formed thereat. The one or more characteristics and the measured angle are utilized by the device to measure the blood analyte level of the user.

The device further comprises a control unit in signal communication with the measuring arrangement to receive value of the measured angle of the polarized filter at the target position with respect to the base position thereof, and in signal communication with the sensor to receive the block signal indicative of the blockage of the light beam thereat, wherein the control unit is configured to determine the at least one blood analyte level in the said body part of the user based on a value of the measured angle of the polarized filter at the target position thereof in response to receipt of the block signal. Typically, upon measuring the angle of the polarized filter via the measuring arrangement and the receipt of the block signal via the sensor, the control unit is configured to determine the at least one blood analyte level in the said body part of the user based on a value of the measured angle of the polarized filter at the target position thereof in response to receipt of the block signal. The control unit is operable to control operation of the one or more components such as, the filtering unit, the sensor, the measuring arrangement, the light arrangement either automatically or based on an input from the user. The control unit includes a combination of hardware and software components configured to determine the at least one blood analyte level of the user. For example, the control unit may include at least one of a processor, memory and input/output peripherals and software to be executable by the processor and stored in the memory.

Optionally, the control unit is operable to receive and transmit instructions in the form of control signals. The term 'control signal' refers to a pulse or frequency of electricity or light that carries data for a control command as it travels over a network, a computer channel or wireless. The processor refers to a computational element that is operable to respond to and processes instructions that drive the device. In an embodiment, the processor includes, but is not limited to, a microprocessor, a microcontroller, a complex instruction set computing (CISC) microprocessor, a reduced instruction set (RISC) microprocessor, a very long instruction word (VLIW) microprocessor, or any other type of processing circuit. The memory as used herein refers to a volatile or persistent medium, such as an electrical circuit, magnetic disk, virtual memory or optical disk, in which a computer can store data or software for any duration. In an embodiment, the memory is non-volatile mass storage such as physical storage media. Furthermore, a single memory may encompass and, in a scenario, in case the device is distributed, the processing, memory and/or storage capability may be distributed as well. The I/O device may be utilized to analyze or display the blood analyte levels by domain experts. In some embodiments, the display unit may be a part of the I/O device.

In one or more embodiments, the control unit is configured to determine the at least one blood analyte level in the said body part of the user as normal when the value of the measured angle is about 52.76 degrees in response to the receipt of the block signal. The blood analyte level may be measured with respect to a predefined base angle i.e., a predetermined angle of the polarization filter defining a normal blood analyte level for any user (determined from various experiments and observations). Herein, the predefined base angle is substantially 52.76 degrees, and relates to the angle of molar absorbance of glucose, at a given wavelength (such as the first wavelength). For example, a predefined base angle of 52.76 degrees may vary from 47 degrees, 48 degrees, 49 degrees, 50 degrees, 51 degrees, 52 degrees, 52.5 degrees, 52.6, 52.7 degrees up to 52 degrees, 52.75 degrees, 52.8 degrees, 52.9 degrees, 53 degrees, 54 degrees, 55 degrees, 56 degrees, 57 degrees.

In operation, the control unit utilizes the received value of the measured angle of the polarized filter at the target position with respect to the base position thereof, and the block signal indicative of the blockage of the light beam thereat, to determine the blood analyte level based on the formula:

$$\text{Blood Analyte Level } (BAL) = \frac{(\text{measured angle} \times 100)}{I} \times \frac{W}{\varepsilon} = \frac{(\text{measured angle} \times 100 \times 859)}{(59.26 \times 430.15)}$$

Herein, 'I' refers to the index averages of analyte being measured such as, glucose, sucrose, and fructose, 'W' refers to the first wavelength of light beam, 'ε' refers to a molar extinction coefficient of glucose.

Herein, the measured angle of the polarized filter at the target position is divided by the predefined base angle of 52.76 degrees, to derive a percentage value of absorbance. Moreover, depending on the type of analyte to be measured via the device, the resulting value is divided by a Molar Extinction Coefficient of Glucose determined to be 430.15 and multiplied by 0.001 meters i.e., average distance travelled by the light beam passing through the body part of the user while being measured via the device. Beneficially, the control unit is able to determine the blood analyte level including both, blood sugar, and HbgA1c values of the user equal to the conventional finger stick method, without the pain and blood in a quick and effective manner.

In one or more embodiments, the control unit is configured to calibrate the measured blood analyte level in range of −10% to +10% based on one or more previously obtained blood analyte levels for the same user. Typically, upon determining the blood analyte level of the user, the control unit may calibrate the determined levels in the range of −10% to +10% based on previous history of the user i.e., based on the one or more previously obtained blood analyte levels for the same user, or other users with similar medical profiles.

In one or more embodiments, the device further comprises an optical lens configured to concentrate the light beam passing through the polarized filter at the sensor. The light beam upon passing through the body part of the user is partially absorbed and/or diffracted in multiple directions weakening the incoming light beam and thus the optical lens is placed before the sensor to beneficially concentrate the light beam onto the sensor for enabling accurate detection of the light beam and the blockage by the polarized filter and consequently an accurate determination of the at least one blood analyte level of the user.

In one or more embodiments, the device further comprises a display unit communicably coupled to the control unit to receive the determined at least one blood analyte level and configured to display the received at least one blood analyte level of the user. Typically, upon determining the at least one blood analyte level, the control unit is configured to transmit the determined at least one blood analyte level to the display unit for display thereat and enable the user to monitor the blood analyte levels upon requirement.

In one or more embodiments, the device further comprises a battery unit configured to provide electrical power to one or more of: the light arrangement, the filtering unit, the measuring arrangement, the sensor, the control unit. To measure the at least one blood analyte level of the user, the device further comprises the batter unit configured for providing the electrical power to the devices and the components therein to operate. Optionally, the measuring arrangement and the filtering arrangement comprises only mechanical components that do not require electrical power to operate i.e., in a manual device for measuring blood analyte levels and thereby reduces the required electrical consumption via the device. Optionally, the measuring arrangement and the filtering arrangement comprises both mechanical and electrical components that additionally requires the electrical power from the battery unit to enable the device to operate automatically i.e., without any intervention from the user.

DETAILED DESCRIPTION OF THE DRAWINGS

Referring to FIG. 1, illustrated is an exemplary schematic illustration of a device 100 for non-invasive measurement of at least one blood analyte level in a user, in accordance with various embodiments of the present disclosure. As shown, the device 100 comprises a light arrangement 102 configured to emit a light beam, the light arrangement 102 adapted to be arranged to emit the light beam towards a body part S of the user. Further, optionally, the device 100 comprises a polarized filter 104 adapted to be arranged to receive the light beam to filter at least a portion of the received light beam. The polarized filter 104 refers to a type of optical filter configured to selectively pass the emitted light beam having a specific polarization. Optionally, based on requirements of the implementation of the device 100, at least one of an intensity or a wavelength of the emitted light beam is varied, to achieve a specific wavelength or intensity required for the implementation and at the same time removes the need of the polarized filter 104 to make the device 100 lighter and more efficient. The device 100 further comprises a filter modulator 106 configured to be displaced between a base position and a target position, wherein the filter modulator 106 is configured to block the light beam received (directly or indirectly) from the light arrangement 102 at the base position thereof and to block the light beam received after passing through the body part S of the user at the target position thereof, Optionally, the device 100 further comprises an optical lens 108 configured to concentrate the light beam passing through the filter modulator 106. Furthermore, the device 100 comprises a sensor 110 arranged to receive the light beam passed through the filter modulator 106, the sensor 110 configured to generate a block signal in response to blockage of the light beam to be received thereat. Moreover, in some embodiments, the optical filter 104 and the filter modulator 106 may be arranged next to the sensor 110. Furthermore, the device 100 is configured to measure value of an angle of the filter modulator 106 at the target position with respect to the base position thereof and employ the block signal indicative of the blockage of the light beam thereat, to determine the at least one blood analyte level in the said body part S of the user based on the value of the measured angle of the filter modulator 106 at the target position thereof.

Figure 2A:
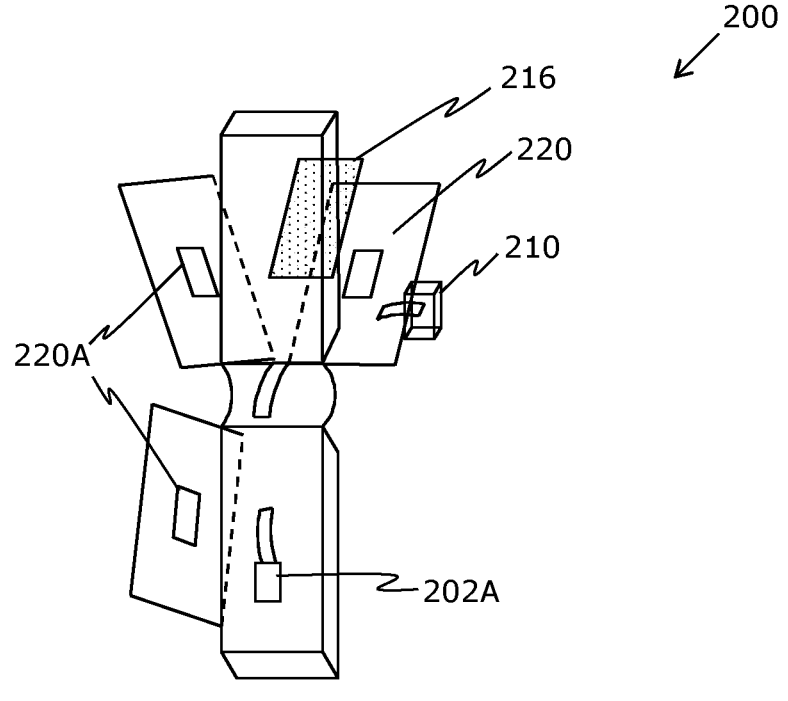
FIGS. 2A and 2B illustrate diagrammatic views of the device for non-invasive measurement of at least one blood analyte level in a user, in accordance with various embodiments of the present disclosure.
Figure 2B:
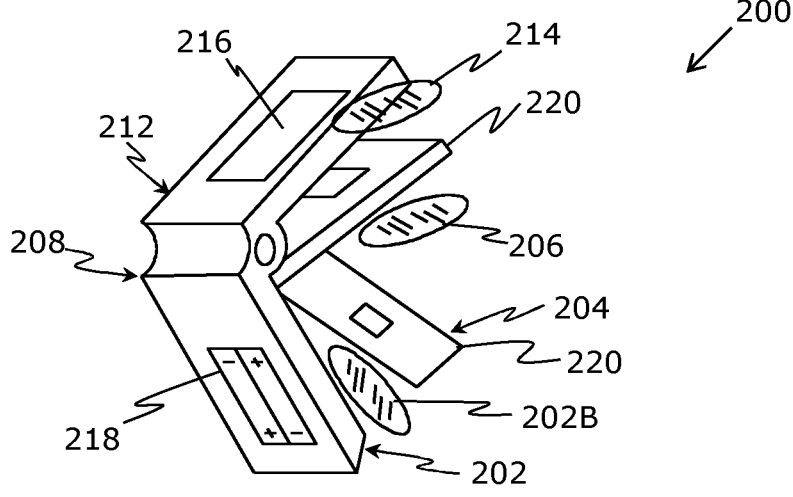

Referring to FIGS. 2A and 2B, in combination, illustrated are diagrammatic views of a device 200 for non-invasive measurement of at least one blood analyte level in a user, in accordance with various embodiments of the present disclosure. Herein, FIGS. 2A and 2B illustrate different positional variations and parts of the device 200. As shown in FIGS. 2A and 2B, the device 200 comprises a light arrangement 202 configured to emit a light beam with a first wavelength, the light arrangement 202 adapted to be arranged to emit the light beam towards a body part of the user. Optionally, the light arrangement 202 comprises at least one light source 202A configured to emit a spectrum of electromagnetic radiation and a filter 202B configured selectively pass the light beam from the spectrum of electromagnetic radiation with the first wavelength. Further, the device 200 comprises a filtering unit 204 adapted to be arranged to receive the light beam passed through the body part of the user. The filtering unit 204 comprises a polarized filter 206 configured to be displaced between a base position and a target position, wherein the filtering unit 204 is configured to block the light beam received directly from the light arrangement 202 at the base position thereof and to block the light beam received after passing through the body part of the user at the target position thereof. Furthermore, the device 200 comprises a measuring arrangement 208 configured to measure an angle of the polarized filter 206 at the target position with respect to the base position thereof. Furthermore, the device 200 comprises a sensor 210 arranged to receive the light beam passed through the polarized filter 206, the sensor 210 configured to generate a block signal in response to blockage of the light beam to be received thereat. Furthermore, the device 200 comprises a control unit 212 in signal communication with the measuring arrangement 208 to receive value of the measured angle of the polarized filter 206 at the target position with respect to the base position thereof, and in signal communication with the sensor 210 to receive the block signal indicative of the blockage of the light beam thereat, wherein the control unit 212 is configured to determine the at least one blood analyte level in the said body part S of the user based on a value of the measured angle of the polarized filter 206 at the target position thereof in response to receipt of the block signal. The device 200 further comprises an optical lens 214 configured to concentrate the light beam passing through the polarized filter 206 at the sensor 210 and a display unit 216 communicably coupled to the control unit 212 to receive the determined at least one blood analyte level and configured to display the received at least one blood analyte level of the user. Furthermore, the device 200 further comprises a battery unit 218 configured to provide electrical power to one or more of: the light arrangement 202, the filtering unit 204, the measuring arrangement 208, the sensor 210, the control unit 212. Optionally, the device 200 further comprises at least one elastic member 220 comprising one or more orifices 220A for allowing passage of the light beam from the light arrangement 202 to the sensor 210. The at least one elastic member 220 completely blocks the incident light beam except from the one or more orifices 220A arranged at the light arrangement 202 and the sensor 210 based on the implementation of the device 200.

Figure 3:
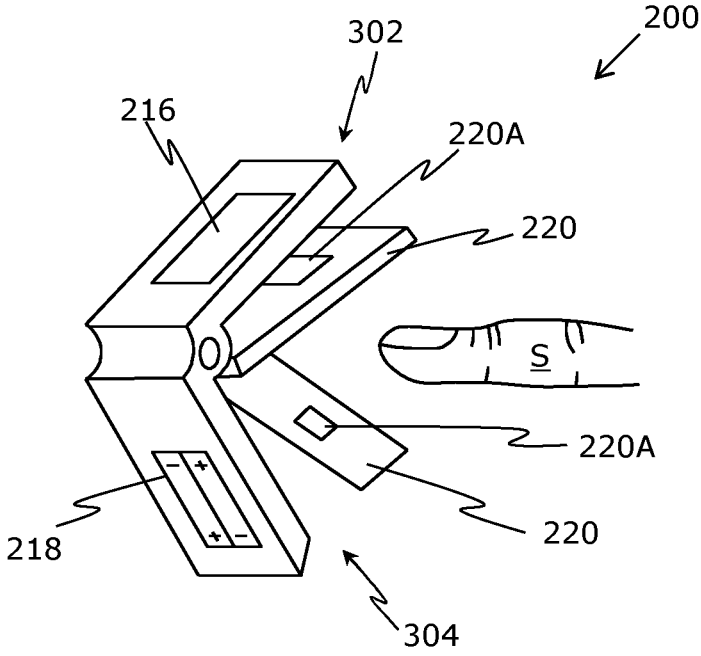
FIG. 3 illustrates an exemplary depiction of implementation of a device for non-invasive measurement of at least one blood analyte level in a body part of the user, in accordance with various embodiments of the present disclosure.

Referring to FIG. 3, illustrated is an exemplary depiction of implementation of the device 200 for measuring the at least one blood analyte level in a body part S of the user, in accordance with various embodiments of the present disclosure. As shown, the body part S of the user is accommodated by the device 200 to measure the at least one blood analyte level of the user. Herein, the body part S of the user is accommodated between the two portions of the device 200 i.e., a first portion 302 and a second portion 304 and wherein the body part S of the user is at least one of an eye, an ear lobe, a finger, a penis. Typically, the first portion 302 comprises at least one of the polarized filter 206 of the filtering unit 204, the control unit 212, the optical lens 214, the display unit 216 and the sensor 210; whereas the second portion 304 comprises at least the light arrangement 202 and the battery unit 218. The measuring arrangement 208 and the motor arrangement (not shown) of the filtering unit 204 may be interchangeably located in either one of the first portion 302 and the second portion 304 based on the available room inside the device 200. Moreover, each of the first portion 302 and the second portion 304 may comprises the elastic member 220 comprising the one or more orifices 220A (i.e., for each of the light arrangement 202 and the sensor 210) enabling passage of the light beam therethrough.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A device for non-invasive measurement of at least one blood analyte level in a user, the device comprising:
   a light arrangement configured to emit a light beam with a first wavelength, the light arrangement adapted to be arranged to emit the light beam towards a body part of the user;
   a filtering unit adapted to be arranged to receive the light beam passed through the body part of the user, the filtering unit comprising a polarized filter configured to be displaced between a base position and a target position, wherein the filtering unit is configured to block the light beam received directly from the light arrangement at the base position thereof and to block the light beam received after passing through the body part of the user at the target position thereof;
   a measuring arrangement configured to measure an angle of the polarized filter at the target position with respect to the base position thereof;
   a sensor arranged to receive the light beam passed through the polarized filter, the sensor configured to generate a block signal in response to blockage of the light beam to be received thereat; and
   a control unit in signal communication with the measuring arrangement to receive value of the measured angle of the polarized filter at the target position with respect to the base position thereof, and in signal communication with the sensor to receive the block signal indicative of the blockage of the light beam thereat,
   wherein the control unit is configured to determine the at least one blood analyte level in the said body part of the user based on a value of the measured angle of the polarized filter at the target position thereof in response to receipt of the block signal;
   wherein the filtering unit further comprises a motor arrangement configured to displace the polarized filter between the base position and the target position thereof;
   wherein the motor arrangement is configured to displace the polarized filter by performing at least one of an angular displacement or a linear displacement of the polarized filter; and
   wherein the polarized filter is displaced by an angular displacement of 0 degree and/or a linear displacement of 0 millimeter at the base position.

2. A device for non-invasive measurement of at least one blood analyte level in a user, the device comprising:
   a light arrangement configured to emit a light beam with a first wavelength, the light arrangement adapted to be arranged to emit the light beam towards a body part of the user;
   a filtering unit adapted to be arranged to receive the light beam passed through the body part of the user, the filtering unit comprising a polarized filter configured to be displaced between a base position and a target position, wherein the filtering unit is configured to block the light beam received directly from the light arrangement at the base position thereof and to block the light beam received after passing through the body part of the user at the target position thereof;
   a measuring arrangement configured to measure an angle of the polarized filter at the target position with respect to the base position thereof;
   a sensor arranged to receive the light beam passed through the polarized filter, the sensor configured to generate a block signal in response to blockage of the light beam to be received thereat; and
   a control unit in signal communication with the measuring arrangement to receive value of the measured angle of the polarized filter at the target position with respect to the base position thereof, and in signal communication with the sensor to receive the block signal indicative of the blockage of the light beam thereat,
   wherein the control unit is configured to determine the at least one blood analyte level in the said body part of the user based on a value of the measured angle of the polarized filter at the target position thereof in response to receipt of the block signal;
   wherein the filtering unit further comprises a motor arrangement configured to displace the polarized filter between the base position and the target position thereof;
   wherein the motor arrangement is configured to displace the polarized filter by performing at least one of an angular displacement or a linear displacement of the polarized filter; and
   wherein the polarized filter is displaced by an angular displacement in a range of 0 degree to 90 degrees and/or a linear displacement in the range of 0 millimeters to 50 millimeters at the target position.

3. A device for non-invasive measurement of at least one blood analyte level in a user, the device comprising:

a light arrangement configured to emit a light beam with a first wavelength, the light arrangement adapted to be arranged to emit the light beam towards a body part of the user;

a filtering unit adapted to be arranged to receive the light beam passed through the body part of the user, the filtering unit comprising a polarized filter configured to be displaced between a base position and a target position, wherein the filtering unit is configured to block the light beam received directly from the light arrangement at the base position thereof and to block the light beam received after passing through the body part of the user at the target position thereof;

a measuring arrangement configured to measure an angle of the polarized filter at the target position with respect to the base position thereof;

a sensor arranged to receive the light beam passed through the polarized filter, the sensor configured to generate a block signal in response to blockage of the light beam to be received threat; and a control unit in signal communication with the measuring arrangement to receive value of the measured angle of the polarized filter at the target position with respect to the base position thereof, and in signal communication with the sensor to receive the block signal indicative of the blockage of the light beam thereat, wherein the control unit is configured to determine the at least one blood analyte level in the said body part of the user based on a value of the measured angle of the polarized filter at the target position thereof in response to receipt of the block signal; and wherein the control unit is configured to determine the at least one blood analyte level in the said body part of the user as normal when the value of the measured angle is about 52.76 degrees in response to the receipt of the block signal.

4. The device according to claim 3, wherein the control unit is configured to calibrate the measured blood analyte level in range of −10% to +10% based on one or more previously obtained blood analyte levels for the same user.

* * * * *